United States Patent [19]

Mulder et al.

[11] 4,237,322

[45] Dec. 2, 1980

[54] PROCESS FOR PREPARATION OF 1,5-DIMETHYLBICYCLO[3,2,1]OCTAN-8-OL

[75] Inventors: Albertus J. Mulder; Aaldert J. de Jong, both of Amsterdam, Netherlands

[73] Assignee: Shell Oil Company, Houston, Tex.

[21] Appl. No.: 37,195

[22] Filed: May 8, 1979

[30] Foreign Application Priority Data

May 12, 1978 [NL] Netherlands .......................... 7805142

[51] Int. Cl.³ .............................................. C07C 35/24
[52] U.S. Cl. ....................................... 568/820; 560/20; 560/72; 560/84; 560/107; 560/194; 560/256; 260/465.4

[58] Field of Search .................. 568/820; 560/256, 20, 560/72, 84, 107

[56] References Cited
PUBLICATIONS

Cope et al., J.A.C.S. 82, 4299–4307, (1960).

Primary Examiner—Paul J. Killos

[57] ABSTRACT

A process for the preparation of 1,5-dimethylbicyclo[3,2,1]octan-8-ol is described wherein 1,5-dimethyl-1,5-cyclooctadiene is reacted with a carboxylic acid in the optional presence of acid catalyst to form the corresponding ester of 1,5-dimethylbicyclo[3,2,1]-octan-8-ol which is subsequently hydrolyzed or alcoholyzed to the alcohol product.

10 Claims, No Drawings

PROCESS FOR PREPARATION OF 1,5-DIMETHYLBICYCLO[3,2,1]OCTAN-8-OL

BACKGROUND OF THE INVENTION

The invention relates to a new process for preparation of 1,5-dimethylbicyclo[3,2,1]octan-8-ol. More particularly, this invention is directed to a stepwise synthesis technique by which 1,5-dimethylbicyclo[3,2,1]octan-8-ol can be prepared in good yields from readily available starting materials.

1,5-Dimethylbicyclo[3,2,1]octan-8-ol is a compound having high thermal stability which can be used to advantage as a starting material for preparing additives for lubricating oil such as those described in copending U.S. patent application Ser. No. 883,761, filed Mar. 6, 1978. (Common assignee). Further, the compound is also useful as a base material for the preparation of aroma chemicals.

The preparation of 1,5-dimethylbicyclo[3,2,1]octan-8-ol has been described in the literature. Specifically, it is disclosed by J. K. Whitesell, R. S. Matthews and P. A. Solomon in Tetrahedron Letters No. 19, pp. 1549–1552, 1976 that 1,5-dimethylbicyclo[3,2,1]octan-8-ol can be obtained in yield of 50% by reacting 1,5-dimethyl-1,5-cyclooctadiene with a solution of perchloric acid in a mixture of water and dioxane. However, the handling of perchloric acid presents safety hazards and other practical drawbacks. Accordingly, it would be of advantage if a technique could be developed for the preparation of 1,5-dimethylbicyclo[3,2,1]octan-8-ol which uses readily available and easily handleable starting materials while providing good yields of the desired alcohol product.

SUMMARY OF THE INVENTION

In accordance with the present invention, it has now been found that 1,5-dimethylbicyclo[3,2,1]octan-8-ol can be readily prepared in high yields by reacting 1,5-dimethyl-1,5-cyclooctadiene with a carboxylic acid of the general formula R—COOH selected from the class consisting of:

(a) carboxylic acids having a pK value below about 4 wherein R in the general formula above is hydrogen, a carboxyl group, or an aliphatic, cycloaliphatic or aromatic group of up to eight carbon atoms substituted with one or more halogen atoms, carboxyl, hydroxyl, cyano or nitro groups and (b) carboxylic acids having a pK value above about 4 wherein R in the general formula above is an unsubstituted aliphatic, cycloaliphatic or aromatic group of up to 8 carbon atoms;

said reaction with carboxylic acids in subclass (b) being further carried out in the presence of an acid catalyst, to afford an ester of 1,5-dimethylbicyclo[3,2,1]octan-8-ol and the carboxylic acid used followed by hydrolysis or alcoholysis of the ester to yield 1,5-dimethylbicyclo[3,2,1]octan-8-ol.

If desired, the reaction with carboxylic acids having pK values below 4 can be also be carried out in the presence of an acid catalyst to enhance reaction rates and yields. Accordingly, the optional use of an acid catalyst with carboxylic acids of subclass (a) above forms another embodiment of the present invention. In addition to providing higher yields of 1,5-dimethylbicyclo[3,2,1]octan-8-ol than have heretofore been available, the present invention is advantageous in that mixtures of dimethylcyclooctadiene isomers available from industrial sources can be used, that is mixtures of 1,5-and 1,6-dimethyl-1,5-cyclooctadiene obtained via dimerization of isoprene, since the ester forming reaction is selective for the 1,5-dimethyl-1,5-cyclooctadiene starting material.

DESCRIPTION OF THE PREFERRED EMBODIMENTS

The ester forming reaction in the process according to the invention may be carried out with or without the added presence of an acid catalyst depending on the pK value of the carboxylic acid reactant. If the pK value of the carboxylic acid (R—COOH) is less than four, the reaction can be suitably performed in the absence of a catalyst. Very good results are obtained with formic acid. Other suitable carboxylic acids with a pK value less than 4 include, aliphatic, cycloaliphatic and aromatic carboxylic acids, with, preferably, not more than 8 carbon atoms which are substituted with one or more halogen atoms or carboxyl, hydroxyl, cyano or nitro groups. Aliphatic carboxylic acids with from 2 to 5 carbon atoms which are substituted with one or more halogen atoms, such as e.g. mono-, di-, and trifluoroacetic acid and mono-, di-, and trichloracetic acid are preferred. Examples of other suitable carboxylic acids with pK value less than 4 are oxalic acid, cyanobutyric acid, chlorobenzoic acid, phthalic acid, nitrobenzoic acid and hydroxybenzoic acid.

Carboxylic acids with a pK value greater than 4, such as the aliphatic carboxylic acids with two or more carbon atoms do not generally react with 1,5-dimethyl-1,5-cyclooctadiene. However, these acids, preferably aliphatic carboxylic acids with from 2 to 8, in particular from 2 to 5 carbon atoms, can be used in the presence of an acid catalyst, such as for instance sulfuric acid, phosphoric acid, p-toluene-sulfonic acid, or, preferably, an acidic ion-exchange resin, such as for instance the strongly acidic macroreticular cation-exchange resin "AMBERLYST" 14.

The reaction of the 1,5-dimethyl-1,5 cyclooctadiene with the acid carboxylic is generally conducted at temperatures between 0° C. and 150° C. This reaction may be carried out neat or in the presence of a solvent such as for example $CH_2CL_2$, $CHCl_3$, $CCl_4$, benzene, toluene, xylene or nitromethane.

Particularly good results are obtained by heating 1,5-dimethyl-1,5-cyclooctadiene with formic acid to a temperature between 40° and 100° C. It is preferred to use an excess of formic acid, for example 2 to 10 mol per mol dimethylcyclooctadiene. The excess of formic acid may be distilled off after the reaction and the residue by hydrolyzed or alcoholyzed. If desired, the formate of 1,5-dimethylbicyclo[3,2,1]octan-8ol may first be isolated by conventional techniques, but this is not essential to the process of the invention.

Although it is preferred to use formic acid with a water content of from 0 to 10%w, it is possible to use formic acid with a higher water content of from 10 to 40%w, in particular if a phase transfer catalyst such as tri-sec. octyl-methylammonium chloride ("ALIQUAT") is added to the reaction mixture.

Since both the preparation of the formate and the hydrolysis or alcoholysis of the ester formed proceed virtually quantitvely, a much higher yield of 1,5-dimethylbicyclo[3,2,1]octanol-8 can be obtained with the process according to the invention than with the known process.

As mentioned above, a suitable starting material in the new process is a mixture consisting of 1,5- and 1,6-dimethyl-1,5-cyclooctadiene, which according to French Pat. specification No. 1,283,217 can be obtained by dimerization of isoprene. The presence of 1,6-dimethyl-1,5-cyclooctadiene in the reaction mixture does not interfere with the formation of the desired ester or its separation from the reaction mixture.

The hydrolysis or alcoholysis of the carboxylic acid ester of 1,5-dimethylbicyclo[3,2,1]octan-8-ol can be carried out using conventional methods. The hydrolysis may, for example, be carried out by refluxing the ester with an aqueous solution of an acid or a base. Especially good results can be obtained by boiling the ester with a solution of a hydroxide of an alkali or alkaline-earth metal, in a mixture of water and an alcohol such as methanol or ethanol. The alcoholysis may, for example, be effected by boiling the ester with a solution of an alcoholate of an alkali metal or alkaline-earth metal in an absolute alcohol, such as methanol or ethanol.

The esters of 1,5-dimethylbicyclo[3,2,1]octan-8-ol with the carboxylic acid R—COOH which are obtained as intermediate products in the process according to the invention are new compounds. Esters derived from carboxylic acids R—COOH, where R represents an aliphatic or an aromatic hydrocarbon group, optionally substituted with an amino group, are aroma chemicals which are the subject of our copending U.S. Patent application Ser. No. 037196 filed May 8, 1979 (common assignee).

EXAMPLE I (A) Preparation of the formate of 1,5-dimethylbicyclo-[3,2,1]octan-8-ol An amount of 420 ml. (11.46 mol) 98–100% formic acid was introduced into a round-bottom flask and, with vigorous stirring, 430 ml (2.74 mol) dimethyl-1,5-cyclooctadiene (a mixture of 80%w 1,5-dimethyl-1,5-cyclooctadiene and 20%w 1,6-dimethyl-1,5-cyclooctadiene) was added to the formic acid at a temperature of 60° C. over a period of 1.5 hours. At the end of this addition period, the conversion of the dimethylcyclooctadiene was complete. Subsequently, 90% of the formic acid was distilled off in vacuum at 60° C. followed by distillation of a bicycle olefin reaction product. This bicyclic olefin distillation product was isolated by extraction with pentane. The residue was taken up in 200 ml pentane and washed with water and an aqueous solution of NaHCO$_3$. After being dried over Na$_2$SO$_4$ the pentane was distilled off and the residue was subjected to fractional distillation in a vacuum. The yield of the formate of 1,5-dimethylbicyclo[3,2,1]octan-8-ol, boiling point 68° C. at 133 Pa (pascal), was 392 g (2.15 mol; 97% calculated on 1,5-dimethyl-1,5-cyclooctadiene). By means of gas chromatography, the purity was shown to be higher than 99%. The product was identified by measurement of the infra-red spectrum and the NME spectrum. Infra-red spectrum: 1000, 1185 and 1730 cm$^{-1}$. The formate consisted of 92%w syn- and of 8%w antiisomer.

When the experiment was repeated with formic acid containing 10%w water, the formate yield was 94.8% calculated on 1,5-dimethyl-1,5-cyclooctadeine. Further, the use of formic acid with an even higher water content (40%w) was found to require addition of a phase transfer catalyst (ALIQUAT) to give reasonable yields.

(B) Preparation of 1,5-dimethylbicyclo[3,2,1]octan-8-ol (1) by hydrolysis

An amount of 182 g of the formate of 1,5-dimethylbicyclo-[3,2,1]octan-8-ol was dissolved in 100 ml methanol and the solution was slowly added to a mixture of 50 g NaOH, 50 ml H$_2$O and 200 ml methanol. After the exothermal reaction was finished, the product was refluxed for 10 minutes. The methanol was distilled off in vacuum and pentane was added to the residue. After washing with water and drying over Na$_2$SO$_4$ 152 g crystalline 1,5-dimethylbicyclo[3,2,1]octan-8-ol (melting point 43° C.) was obtained in quantitative yield by concentrating and cooling the pentane solution. The structure was confirmed by measuring the infra-red and NMR spectra. The weights of syn and antiisomer were in the ratio of 92:8.

(2) by alcoholysis

An amount of 8.8 g of the formate 1,5-dimethylbicyclo[3,2,1]octan-8-ol was dissolved in 50 ml absolute methanol and 10 gm sodium was added to the solution. After refluxing for four hours, methanol and the methyl were taken up into pentane. The solution was washed with water and dried over Na$_2$SO$_4$. Distilling off the pentane yield 6 g of crystalline product with a purity higher than 98%.

EXAMPLE II (A) Preparation of the acetate of 1,5-dimethylbicyclo-[3,2,1]octan-8-ol (a) An amount of 20.4 g dimethyl-1,5-cyclooctadiene (a mixture of 80%w 1,5-dimethyl-1,5-cyclootadiene and 20%w 1,6-dimethyl1,5-cyclooctadiene) was dissolved in 100 ml acetic acid and, after addition of 2 g "AMBERLYST" 15, was refluxed with vigorous stirring. After six hours the conversion was 98%. The reaction mixture was filtered, diluted with water and extracted with pentane. The pentane solution was washed with water and with an aqueous NaHCO$_3$ solution after-which is was dried, evaporated and fractionally distilled. The yield of the desired acetate was 53.3%. The weight of syn and antiisomer were in the ratio of 85:15.

(b) An amount of 13.6 g (0.1 mol) dimethyl-1,5-cyclooctadiene (a mixture of 80%w 1,5-dimethyl-1,5-cyclooctadiene and 20%w 1,6-dimethyl-1,5cyclooctadiene) was dissolved in 60 ml acetic acid. The solution was cooled to 12° C. and 0.5 ml H$_2$SO$_4$ was added dropwise with vigorous stirring. While this was being done the temperature increased to 39° C. After another two hours at room temperature the conversion of the dimethylcyclooctadiene was 98% and the reaction mixture was worked up in the way described under (a). The yield of the desired acetate was 24%. The weights of syn and antiisomer were in the ratio of 85:15.

(B) Preparation of 1,5-dimethylbicyclo[3,2,1]octan-8-ol

A solution of 13.2 g KOH in 10 ml water and 90 ml methanol was added to a solution of 19.6 g of the acetate of 1,5-dimethyl-bicyclo[3,2,1]octan-8-ol in 50 ml methanol. The mixture was refluxed for two hours. The methanol was then distilled off and water and pentane were added to the residue. The pentane layer was washed with water and dried over Na$_2$SO$_4$. Concentration of the pentane solution gave a crystalline product with a melting point of 43° C. The yield was quantitative.

EXAMPLE III

An amount of 136 g dimethyl-1,5-cyclooctadiene (a mixture of 80%w 1,5-dimethyl-1,5-cyclooctadiene and 20%w 1,6-dimethyl-1,5-cyclooctadiene) was added over a period of 30 minutes with stirring to 178 g trichloroacetic acid. During this addition period an ice bath was employed to maintain the reaction temperature below 25° C. The ice bath was then removed and the stirring continued for another three hours, during which the temperature increased to 29° C. A solution of 55 g NaOH in 200 ml water was slowly added to the reaction mixture with stirring. The temperature was kept below 20° C. by means of cooling with ice. The mixture obtained was extracted with cyclohexane and the extract was dried over MgSO4. When the solvent was distilled off, a residue of 148 g was obtained which contained 54%w 1,5-dimethylbicyclo[3,2,1]octan-8-ol.

EXAMPLE IV

An amount of 11.4 g trifluoroacetic acid was slowly added, with stirring to an ice-cooled solution of 13.6 g dimethyl-1,5-cyclooctadiene (a mixture of 80%w 1,5-dimethyl-1,5-dimethyl-1,5-cyclooctadiene and 20%w, 1,6-dimethyl-1,5-cyclooctadiene) in 50 g dichloromethane over a period of 35 minutes. The ice was then removed and the reaction mixture, on warming to room temperature, was washed with an aqueous solution of NaHCO3. Drying over MgSO4 and evaporating the reaction mixture yielded 21.2 g residue. A solution of 4 g NaOH in 10 ml water and 5 ml CH3OH were added to 5 g of this residue, during which the temperature increased to 30° C. Working up of the reaction mixture in a manner described in the above Examples after three hours yielded 3.45 g residue consisting of 1,5-dimethyl-bicyclo[3,2,1]octan-8-ol. Infrared spectrum: 1045; 1100; 1430; 2800 and 2840 cm$^{-1}$.

What is claimed is:

1. A process for the preparation of 1,5-dimethylbicyclo-[3,2,1]octan-8-ol which comprises reacting 1,5-dimethyl-1,5-cyclooctadiene with a carboxylic acid of the general formula R—COOH selected from the class consisting of:
    (a) carboxylic acids having a pK value below about 4 wherein R in the general formula above is hydrogen, a carboxyl group, or an aliphatic, cycloaliphatic or aromatic group of up to 8 carbon atoms substituted with one or more halogen atoms, carboxyl, hydroxyl, cyano or nitro groups and
    (b) carboxylic acids having a pK value above about 4 wherein R in the general formula above is an unsubstituted aliphatic, cycloaliphatic or aromatic group of up to 8 carbon atoms; said reaction with carboxylic acids in subclass (b) being further carried out in the presence of an acid catalyst thereby forming an ester of 1,5-dimethylbicyclo[3,2,1]octan-8-ol and the carboxylic acid employed followed by hydrolysis or alcoholysis of the ester to yield 1,5-dimethylbicyclo[3,2,]1]octan-8-ol.

2. The process according to claim 1 wherein the carboxylic acid employed is an aliphatic carboxylic acid of from 2 to 5 carbon atoms substituted with one or more halogen atoms.

3. The process according to claim 1, wherein the carboxylic acid is an aliphatic carboxylic cid with from 2 to 8 carbon atoms and the reaction with 1,5-dimethyl-1,5-cyclooctadiene is carried out in the presence of an acidic ion exchange resin.

4. The process according to claim 1, wherein the reaction of 1,5-dimethyl-1,5-cyclooctadiene with the carboxylic acid R—COOH is carried out at a temperature between 0° and 150° C.

5. The process according to claim 4 wherein the carboxylic acid is formic acid.

6. The process according to claim 5 wherein 1,5-dimethyl-1,5-cyclooctadiene is reacted with formic acid at a temperature between about 40 and about 100° C.

7. The process according to claim 6, wherein 2 to 10 mol formic acid are used per mol 1,5-dimethyl-1,5-cyclooctadiene.

8. A process according to claim 7, wherein formic acid with a water content of from 0 to 10%w is used.

9. The process according to claim 7 wherein formic acid with a water content of from 10 to 40% in the presence of a phase transfer catalyst is used.

10. The process according to claim 1, wherein a mixture consisting of 1,5- and 1,6-dimethyl-1,5-cyclooctadiene which has been obtained by dimerization of isoprene, is used as the starting material.

* * * * *